US006408695B1

(12) United States Patent
Bewlay et al.

(10) Patent No.: US 6,408,695 B1
(45) Date of Patent: Jun. 25, 2002

(54) ULTRASONIC INSPECTION METHOD AND SYSTEM FOR DETECTING CRITICAL FLAWS

(75) Inventors: Bernard Patrick Bewlay, Schenectady; John Broddus Deaton, Jr., Niskayuna; Michael Francis Xavier Gigliotti, Jr., Scotia; Robert Snee Gilmore, Charlton, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/454,189

(22) Filed: Dec. 3, 1999

(51) Int. Cl.$^7$ .............................................. G01N 3/32
(52) U.S. Cl. ...................................................... 73/579
(58) Field of Search ........................... 73/579, 600, 646

(56) References Cited

U.S. PATENT DOCUMENTS

| | | | | |
|---|---|---|---|---|
| 4,026,157 A | * | 5/1977 | Goebbels | 73/434 PS |
| 4,165,649 A | * | 8/1979 | Greer, Jr. | 73/644 |
| 4,435,984 A | * | 3/1984 | Gruber | 73/628 |
| 4,462,257 A | * | 7/1984 | Gerhart et al. | 73/644 |
| 4,539,848 A | * | 9/1985 | Takafuji et al. | 73/599 |
| 4,633,715 A | * | 1/1987 | Monchalin | 73/657 |
| 5,118,464 A | * | 6/1992 | Richardson et al. | 376/252 |
| 5,335,184 A | * | 8/1994 | Hildebrand | 364/507 |
| 5,404,754 A | * | 4/1995 | Wang | 73/602 |
| 5,406,850 A | * | 4/1995 | Bouchard et al. | 73/620 |
| 5,454,045 A | * | 9/1995 | Perkins et al. | 382/181 |
| 5,533,401 A | * | 7/1996 | Gilmore | 73/622 |
| 5,549,002 A | * | 8/1996 | Howard et al. | 73/602 |
| 5,608,814 A | * | 3/1997 | Gilmore et al. | 382/141 |
| 5,906,692 A | * | 5/1999 | Bhowal et al. | 148/671 |

FOREIGN PATENT DOCUMENTS

EP          1 136 582          9/2001

OTHER PUBLICATIONS

Hecht et al., "Nondestructive Determination of Grain Size in Austenitic Sheet by Ultrasonic Backscattering", Sep. 1981, Materials Evaluation, 39, 934–938.*

(List continued on next page.)

*Primary Examiner*—Hezron Williams
*Assistant Examiner*—C D Garber
(74) *Attorney, Agent, or Firm*—Robert P. Santandrea; Noreen C. Johnson

(57) ABSTRACT

An ultrasonic inspection method for inspecting titanium material is provided. The ultrasonic inspection method is capable of detecting critical flaws in the titanium material that may limit titanium material applications. The ultrasonic inspection method comprises fixing at least one of frequency or acoustic entity size of the titanium material as a constant for the ultrasonic inspecting; wherein the frequency that is fixed is selected based on the size of the flaws deemed critical for mechanical performance—including fatigue performance—in the titanium material, and the grain size that is fixed selected based on the size of the flaws deemed critical for mechanical performance—including fatigue performance—in the titanium material; ultrasonic inspecting the titanium material in which the step of ultrasonic inspecting the titanium material generates scattering from microstructural characteristics and features of the titanium material; detecting generated scattering; characterizing the type of detected scattering; and determining if the titanium material comprises critical flaws based on the type of scattering. If the scattering comprises predominantly Rayleigh scattering, the step of determining determines that the titanium material comprises uniform-fine grain titanium, however, if the scattering comprises Rayleigh scattering and other types of scattering, the step of determining determines that the titanium material may comprise critical flaws that may limit applications of the titanium material. The invention also provides a system for implementing the method, as embodied by the invention.

4 Claims, 1 Drawing Sheet

OTHER PUBLICATIONS

Aharoni et al., "Monitoring material grain size by laser–generated ultrasound", Dec. 30, 1991, Applied Physics Letters, 59, 3530–3532.*

Smith, "Ultrasonic materials characterization", Feb. 1987, NDT International, 43–48.*

Serabian, "Frequency and Grain Size Dependency of Ultrasonic Attenuation in Polycrystalline Materials", Mar. 1980, vol. 22, No. 2, 69–70.*

Saniie et al., "Ultrasonic Grain Size Evaluation of Heat–Treated Stainless Steel Samples", Department of Engineering and Comp., Illinois Institute of Technology, 939–946.*

Nagy et al., "Scattering Induced Attenuation of Ultrasonic Backscattering", Department of Welding Engineering, Ohio State University, 1263–1271.*

The Journal of The Acoustical Society of America, Revised Grain–Scattering Formulas and Tables, Emmanuel P. Papadakis, vol. 37, No. 4, pp. 703–710, Apr. 1965.

The Journal of The Acoustical Society of America, Ultrasonic Attenuation Caused by Scattering in Polycrystalline Metals, Emmanuel P. Papadakis, vol. 37, No. 4, pp. 711–717, Apr. 1965.

* cited by examiner

ULTRASONIC INSPECTION METHOD AND SYSTEM FOR DETECTING CRITICAL FLAWS

BACKGROUND OF THE INVENTION

The invention relates to titanium inspection methods and systems. In particular, the invention relates to methods and systems for inspecting titanium using ultrasonic energy in which the detection of flaws that may be critical to applications of the titanium material is enhanced.

Nondestructive evaluation by ultrasonic inspection and ultrasonic inspection testing is a known material testing and evaluation method. Ultrasonic testing typically requires that detectable flaws possess different acoustic behaviors from bulk material under similar ultrasonic inspection. This different behavior permits the ultrasonic inspection to detect flaws, grains, imperfections, and other related microstructural characteristics for a material. While conventional ultrasonic inspection methods and ultrasonic inspection testing may be adequate for detecting some flaws in titanium, these methods may be limited by noise generated in the ultrasonic inspection. For example, some ultrasonic inspection methods may mask or confuse generated noise with flaws, such as but not limited to large undesirable grains, colonies of undesirable titanium grains, and other microstructural characteristics in the titanium material that may limit applications for the titanium material.

Known ultrasonic inspection methods select an ultrasonic inspection frequency based on a flaw size alone. These ultrasonic inspection methods do not rely on the wavelength of the applied ultrasonic inspection energy to determine granular and microstructural characteristics of the material. The wavelength of the ultrasonic inspection energy is important for ultrasonic inspection, since a short wavelength will readily resolve small flaws in titanium materials, in which these small flaws may be flaws that are critical, in other word, flaws that limit the applications of titanium materials.

Thus, in order to determine acceptable titanium materials for certain critical applications, it is desirable to provide an ultrasonic inspection process that accurately determines the nature of noise during ultrasonic inspection. The ultrasonic inspection method should determine if ultrasonic inspection noise is attributed to a defect, such as a critical flaw, in the titanium material, due to noise, or due to other factors.

Therefore, a need exists for an ultrasonic inspection method for determining material characteristics and properties. Further, a need exists for an ultrasonic inspection method for determining processed titanium characteristics and properties and detecting flaws in titanium that may limit applications of the titanium. Furthermore, a need exists for determining material configurations and characteristics for accurate ultrasonic inspection methods that can minimize noise contributions to the ultrasonic inspection and enhance detection of small but "critical" flaws in titanium.

SUMMARY OF THE INVENTION

In one aspect of the invention, an ultrasonic inspection method is provided. The ultrasonic inspection method is capable of detecting critical flaws in the titanium material that may limit titanium material applications. The ultrasonic inspection method comprises fixing at least one of frequency or grain size of the titanium material as a constant for the ultrasonic inspecting; wherein the frequency that is fixed is representative of critical flaws in the titanium material, and the grain size that is fixed is representative of critical flaws in the titanium material; ultrasonic inspecting the titanium material in which the step of ultrasonic inspecting the titanium material generates scattering from microstructural characteristics and features of the titanium material; detecting generated scattering; characterizing the type of detected scattering; and determining if the titanium material comprises critical flaws based on the type of scattering. If the scattering comprises predominantly Rayleigh scattering, which means that the Rayleigh scattering comprises at least a majority of the scattering and dominates other types of scattering, that the step of determining determines that the titanium material comprises uniform-fine grain titanium, however, if the scattering comprises Rayleigh scattering and other types of scattering, the step of determining determines that the titanium material may comprise critical flaws that may limit applications of the titanium material.

In another aspect of the invention, a system for implementing an ultrasonic inspection method, as embodied by the invention is provided. The ultrasonic inspection system is capable of detecting critical flaws in the titanium material that may limit titanium material applications. The ultrasonic inspection system comprises means for fixing at least one of frequency or grain size of the titanium material as a constant for the ultrasonic inspecting; wherein the frequency that is fixed is representative of critical flaws in the titanium material, and the grain size that is fixed is representative of critical flaws in the titanium material; means for ultrasonic inspecting the titanium material in which the means for ultrasonic inspecting the titanium material generates scattering from microstructural characteristics and features of the titanium material; means for detecting generated scattering; means for characterizing the type of detected scattering; and means for determining if the titanium material comprises critical flaws based on the type of scattering. If the scattering comprises predominantly Rayleigh scattering, the means for determining determines that the titanium material comprises uniform-fine grain titanium. However, if the scattering comprises Rayleigh scattering and other types of scattering, the means for determining determines that the titanium material may comprise critical flaws that may limit applications of the titanium material.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
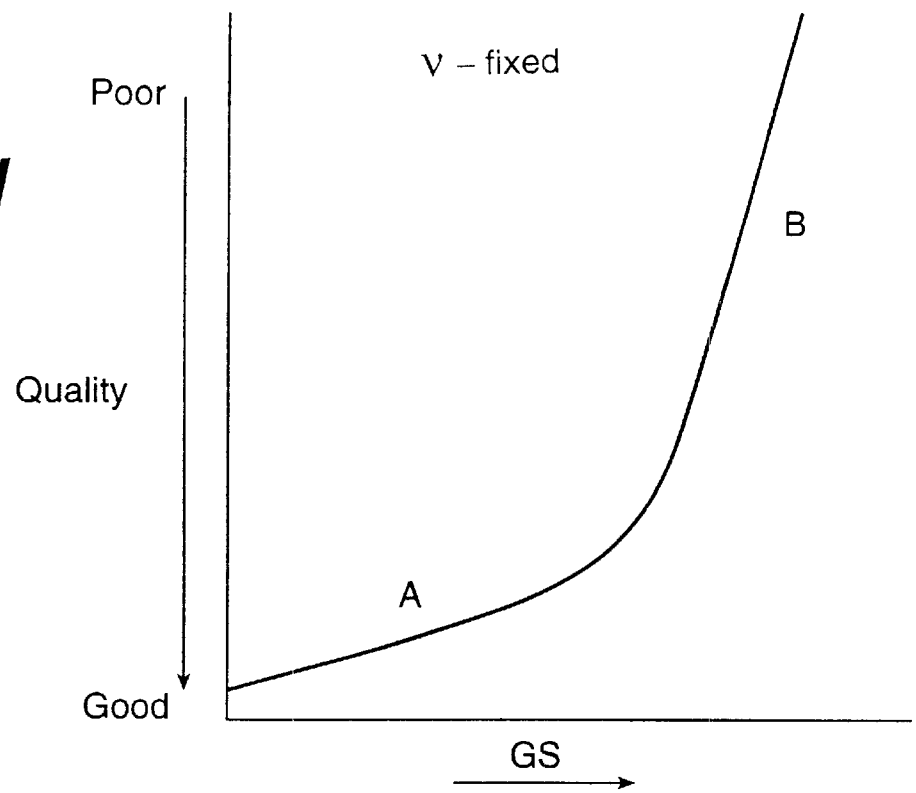
FIG. 1 illustrates generalized graph of material quality (y-axis) versus grain size with frequency fixed.

Ultrasonic inspection can be generalized as inspection of a material by directing ultrasonic energy from an ultrasonic inspection energy source to a material, in which the material is being inspected for flaws, defects, and other such internal discontinuities (hereinafter "flaws"). A "flaw" would also include a discreet colony of $\alpha$Ti particles with common crystallographic orientation within, since this discreet colony could act as site of early mechanical fatigue failure. The ultrasonic energy, such as sound of an appropriate nature, is passed into the material. Reflection or echoes or sound transmitted through the material is sensed, and flaws will reflect the energy and create signals, which can be measured, by appropriate sensors, probes, and associated ultrasonic inspection apparatus and systems. Thus, a size, shape, position, and often the nature of the flaws can be determined.

Ultrasonic inspection techniques have been developed that use focused ultrasonic beams to enhance a flaw fraction within any instantaneously insonified volume of material. These developed ultrasonic inspection techniques can identify indications based both on maximum signal, as well as signal to noise. A scattering of sound in a polycrystalline metallic material body, which is also known in the art as an attenuation of a propagating sound wave, can be described as a function of at least one of grain dimensions, intrinsic material characteristics, and ultrasound frequency. Typically, three different functional relationships among scattering, frequency, and grain dimensions have been described. These are:

for $\lambda > 2\pi D$, $a = Tv^4 \Theta$, termed "Rayleigh" scattering;

for $\lambda < 2\pi D$ or $\lambda \cong D$, $a = Dv^2 \Sigma$, termed "stochastic" or "phase" scattering;

and for $\lambda << D$, $a\ 1/D$, termed "diffusion" scattering;

where a is attenuation, $\lambda$ is wavelength of the ultrasound energy, $v$ is frequency of the ultrasound energy, D is an average grain diameter, T is a scattering volume of grains, and $\Theta$ and $\Sigma$ are scattering factors based on elastic properties of the material being inspected. However, these ultrasonic inspection methods and techniques are not able to accurately detect critical flaws in titanium as they only select an ultrasonic inspection frequency based on flaw size. For the purposes of these relationships, the "grain" is the scattering acoustic entity. If an individual titanium microstructural feature is located in a colony with common crystallographic (and thus elastic) characteristics, the colony dimensions become the "grain" for the above functional relationships.

The microstructure of a material can determine the applications in which the material can be used and the microstructure of a material can limit the applications in which the material can be used. The microstructure can be determined by measuring scattering of sound in a material. The scattering of sound in a material, such as titanium is sensitive to its microstructure. Titanium materials comprising microstructures having uniform-fine grain (UFG) have been determined as suitable and desirable titanium materials for some applications, such as but not limited to use in turbine components. The titanium materials can be provided as uniform-fine grain (UFG) billets and forgings made from UFG billets that comprise fine-scale granular αTi particles. The titanium microstructure's sound scattering sensitivity can be attributed to αTi particles that are arranged into "colonies." These colonies typically have a common crystallographic (and elastic) orientation, and these colonies of αTi particles can behave as large grains in the titanium material.

The size of titanium grains and the nature of αTi particle colony structures may be important variables that influence ultrasonic noise and ultrasonic inspection in single phase and two-phase titanium alloys and materials. Therefore, the size of titanium grains and the nature of αTi particle colony structures may influence ultrasonic inspection techniques, methods, and results by creating undesirable noise during ultrasonic inspection. This noise may hide or mask critical flaws in titanium that may limit applications of the titanium.

While thermomechanical processing techniques, which rely on dynamic recrystallization in the α+β temperature range to achieve uniform fine grain (UFG) αTi particles and prevent colony formation, have been developed to improve titanium microstructure, defects may remain in the titanium material, some of which are difficult to detect using conventional ultrasonic inspection techniques and methods.

The ultrasonic inspection of these uniform-fine grain (UFG) billets and forgings made from UFG billets generally produces predominantly Rayleigh scattering. Scattering characterized as other types of scattering, such as phase scattering, generally indicates that the titanium material includes at least one of grains that are not uniform-fine grain (UFG) and other flaws that may limit the applications of the titanium, and are thus referred to as "critical" flaws. Thus, as embodied by the invention, the ultrasonic inspection to determine if the titanium-containing materials comprise uniform-fine grains are suitable for various microstructurally sensitive applications, is enhanced by determining if scattering is predominantly Rayleigh scattering. If the ultrasonic inspection, as embodied by the invention, determines scattering other than predominantly Rayleigh scattering, for example phase scattering alone or in combination with Rayleigh scattering, it is possible to characterize the material as not being preferred for maximum probability of flaw detection.

For acceptable titanium for turbine component applications, αTi particles in the titanium material are generally less than about 5 µm in diameter, and are generally formed with an absence of crystallographic texture. The ultrasonic inspectability of these UFG titanium materials is characterized by a signal to noise ratio from machined flat bottom holes. The signal to noise ratio obtained by ultrasonic inspection, as embodied by the invention, is greater in UFG titanium materials than in the conventional titanium materials. It has been determined that there is less ultrasonic backscattered noise in the UFG titanium materials than in the conventional titanium materials. Further, it has been determined using ultrasonic inspection, as embodied by the invention, that an ultrasonic signal from machined flat bottomed holes is higher in the UFG titanium material. For titanium materials with αTi particles less than about 10 µm in size, differences in αTi particle size typically do not have a significant effect on generated ultrasonic noise. For example, UFG billets display chiefly Rayleigh scattering, while conventional billets, which are not characterized by UFG properties, display Rayleigh scattering plus phase scattering when subjected to ultrasonic inspection, as embodied by the invention.

Figure 2:
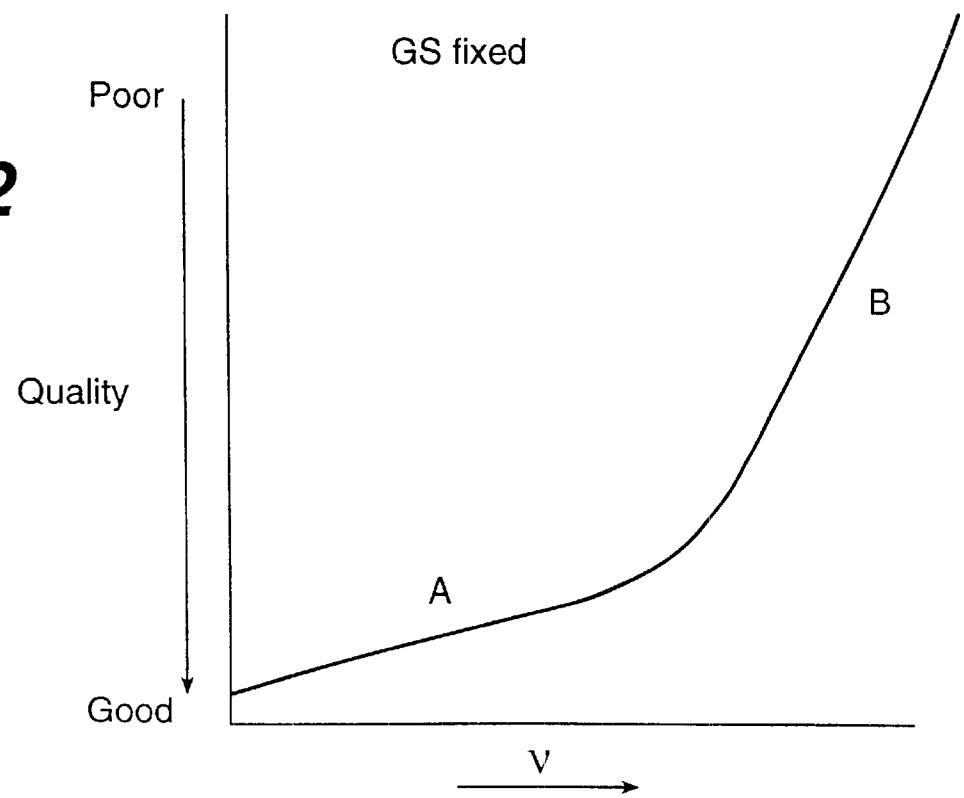
FIG. 2 illustrates another generalized graph of material quality (y-axis) versus frequency with grain size fixed.

The speed of sound, c, is equal to the product of the wavelength, $\lambda$, of an energy and the frequency, $v$, of the energy: $c=\lambda v$. For ultrasonic inspection, as embodied by the invention, FIGS. 1 and 2 illustrate curves representative of generalized relationships between titanium material quality (y-axis) and grain size with the frequency being fixed (FIG. 1) and titanium material quality (y-axis) and frequency with the grain size being fixed (FIG. 2). These figures and curves are exemplary for generalization purposes only and describe the basic relations between quality, grain size, and frequency, and are not intended to limit the invention in any manner. The figures illustrate that for ultrasonic inspection, as embodied by the invention, by fixing a frequency a shift occurs along the curve towards smaller grain sizes (FIG. 1). Similarly, FIG. 2 illustrates that for ultrasonic inspection, as embodied by the invention, by fixing a grains size to be detected, a shift occurs along the curve towards lower frequencies. Thus, a relationship between grain size, frequency, and quality determined by ultrasonic inspection, as embodied by the invention, can be determined. With reference to FIGS. 1 and 2, the functionality of material quality (as defined by ultrasound scattering behavior) as a function of acoustic entity size or ultrasound wavelength varies in a smooth fashion from one regime ("Rayleigh" to "phase" to "diffusion") to another. For adequate inspection to find critical flaws, and to assure predominantly Rayleigh scattering, the acoustic entity size needs to be not greater than about 1/10 the wavelength of the sound used for inspection.

The ultrasonic inspection method, as embodied by the invention, comprises selecting a frequency for ultrasonic inspection for detecting a flaw in a titanium material, in which the flaw may be considered a critical flaw. The ultrasonic inspection method then comprises selecting titanium material entity characteristics that are sufficient for generating Rayleigh scattering predominantly. The titanium material entity characteristics that are sufficient for generating predominantly Rayleigh scattering only comprise at least one of microstructure and crystallographic texture characteristics that will cause the ultrasonic inspection, as embodied by the invention, to generate the Rayleigh scattering only.

The ultrasonic inspection method, as embodied by the invention, comprises providing a titanium material that is subjected to ultrasonic inspection by directing ultrasonic energy onto the titanium material. The ultrasonic energy is provided with a frequency that is selected to enhance the probability of detecting a critical flaw in the titanium material, in which the critical flaw would compromise applications of the titanium.

In FIG. 1, with the frequency, v, fixed, ultrasonic inspection is done at a certain fixed frequency that is selected to detect microstructural flaws, in which these flaws are ones that may be critical to a titanium material's applications. An ultrasonic inspection method, as embodied by the invention, comprises selecting this fixed frequency for detection and resolution of a critical flaw. The ultrasonic inspection is conducted and the ultrasonic inspection method further comprises selecting frequency and material acoustic entity characteristics that are sufficient to result in predominantly Rayleigh scattering from the titanium material, which is in the "A" region of the curve. The material acoustic entity characteristics include, but are not limited to microstructure and crystallographic texture characteristics.

Upon ultrasonic inspection and directing of ultrasonic energy into the titanium material, scattering occurs due to titanium grains and other microstructure in the titanium. If the ultrasonic inspection reveals that there is predominantly Rayleigh scattering, which is in the "A" region of the curve, the ultrasonic inspection and the resultant scattering is indicative of acceptable UFG titanium. Thus, this characteristic Rayleigh scattering is indicative that the titanium material, which comprises a UFG titanium material, is generally acceptable for titanium applications, such as but not limited to turbine components. However, if the resultant scattering includes scattering other than Rayleigh scattering, which is in the "B" region of the curve, the ultrasonic inspection is indicative of flaws in the titanium material, and these flaws may be critical flaws that limit the titanium applications for the material.

FIG. 2 illustrates a quality curve for ultrasonic inspection with a fixed grain size and varying frequency during ultrasonic inspection, as embodied by the invention. The frequency is varied to detect microstructural flaws, in which these flaws are ones that may be critical to a titanium material's applications. An ultrasonic inspection method, as embodied by the invention, comprises selecting a fixed grain size, such as those representative of critical flaws, for detection and resolution. The ultrasonic inspection is conducted, and the ultrasonic inspection method further comprises selecting frequency and material acoustic entity characteristics that are sufficient to result in predominantly Rayleigh scattering from the titanium material, which is in the "A" region of the curve. The material acoustic entity characteristics include, but are not limited to microstructure and crystallographic texture characteristics.

Upon ultrasonic inspection and directing of ultrasonic energy into the titanium material, scattering occurs due to titanium grains and other microstructure in the titanium. If the ultrasonic inspection, as embodied by the invention, reveals that there is predominantly Rayleigh scattering, the ultrasonic inspection and the resultant scattering is indicative of acceptable UFG titanium. Thus, this characteristic Rayleigh scattering is indicative that the titanium material, which comprises a UFG titanium material, is generally acceptable for titanium applications, such as but not limited to turbine components. However, if the resultant scattering includes scattering other than Rayleigh scattering, which is in the "B" region of the curve, the ultrasonic inspection is indicative of flaws in the titanium material, and these flaws may be critical flaws that limit the titanium applications for the material.

The invention is also directed to a system that is capable of implementing the ultrasonic inspection method, as embodied by the invention, in which the invention comprises apparatus, sensors, ultrasonic inspection apparatus, and other means for implementing the invention. For example, and in no way limiting of the invention, the system includes at least one control structure that may comprise any appropriate high-powered solid-state switching device. The control may be a computer. However, this is merely exemplary of an appropriate high-powered control, which is within the scope of the invention. For example but not limiting of the invention, the control for the ultrasonic inspection can comprise at least one of a silicon controlled rectifier (SCR), a thyristor, MOS-controlled thyristor (MCT) and an insulated gate bipolar transistor. The control can be implemented as a single special purpose integrated circuit, such as ASIC, having a main or central processor section for overall, system-level control, and separate sections dedicated performing various different specific combinations, functions and other processes under control of the central processor section. It will be appreciated by those skilled in the art that the control can also be implemented using a variety of separate dedicated or programmable integrated or other electronic circuits or devices, such as hardwired electronic or logic circuits including discrete element circuits or programmable logic devices, such as PLDs, PALs, PLAs or the like. The control can also be implemented using a suitably programmed general-purpose computer, such as a microprocessor or micro-control, or other processor device, such as a CPU or CPU, either alone or in conjunction with one or more peripheral data and signal processing devices.

Ultrasonic inspection methods and systems that are exemplary of the methods and systems for implementing the methods and systems, as embodied by the invention, are described in concurrently filed U.S. Ser. No. 09/454,191, filed Dec. 3, 1999. Descriptions of the ultrasonic inspection methods can be found in the above-referenced application, which is fully incorporated by reference herein.

While various embodiments are described herein, it will be appreciated from the specification that various combinations of elements, variations or improvements therein may be made by those skilled in the art, and are within the cope of the invention.

What is claimed is:

1. A method for ultrasonically inspecting a titanium article for at least one critical flaw that acts as a non-Rayleigh scattering source of ultrasonic radiation, the method comprising the steps of:
   a) selecting a frequency for detecting the at least one critical flaw, the at least one critical flaw being larger than a predetermined dimension;
   b) providing the titanium article, the titanium article having a plurality of acoustic entities that generate only Rayleigh scattering of ultrasonic radiation, wherein each of the plurality of acoustic entities comprises a colony of αTi particles having a common crystallographic orientation;
   c) directing ultrasonic energy of the selected frequency into the bulk of the titanium article;
   d) detecting ultrasonic radiation scattered from the bulk of the titanium article; and
   e) determining whether the ultrasonic radiation scattered is a result of one of predominantly Rayleigh scattering and non-Rayleigh scattering, wherein a determination that the ultrasonic radiation scattered is a result of non-Rayleigh scattering is indicative of the critical flaw.

2. The method according to claim 1, wherein the step of providing the titanium article comprises providing the titanium article, the titanium article comprising a plurality of αTi particles, wherein the plurality of αTi particles is substantially free of crystallographic texture, wherein each of the plurality of αTi particles has a diameter of less than about 10 microns, and wherein the plurality of αTi particles act as acoustic entities that generate only Rayleigh scattering of ultrasonic radiation.

3. A method for determining acceptability of a titanium article, the method comprising the steps of:
   a) selecting a frequency of ultrasonic radiation for detecting at least one critical flaw in the titanium article, the at least one critical flaw being larger than a predetermined dimension;
   b) providing the titanium article, the titanium article having a plurality of acoustic entities that generate only Rayleigh scattering of ultrasonic radiation, wherein each of the plurality of acoustic entities comprises a colony of αTi particles having a common crystallographic orientation;
   c) ultrasonically inspecting the titanium article by directing ultrasonic energy of the selected frequency into the bulk of the titanium article;
   d) detecting ultrasonic radiation scattered from the bulk of the titanium article by the ultrasonic inspection;
   e) determining whether the ultrasonic radiation scattered is a result of one of predominantly Rayleigh scattering and non-Rayleigh scattering, wherein a determination that the ultrasonic radiation scattered is a result of non-Rayleigh scattering is indicative of the critical flaw, and
   f) determining the acceptability of the titanium article, wherein the titanium article is acceptable if the ultrasonic radiation scattered is a result of predominantly Rayleigh scattering, and wherein the titanium article is a result of non-Rayleigh scattering.

4. The method according to claim 3, wherein the step of providing the titanium article comprises providing the titanium article, the titanium article comprising a plurality of αTi particles, wherein the plurality of αTi particles is substantially free of crystallographic texture, wherein each of the plurality of αTi particles has a diameter of less than about 10 microns, and wherein the plurality of αTi particles act as acoustic entities that generate only Rayleigh scattering of ultrasonic radiation.

* * * * *